US007964217B2

(12) United States Patent
Harris

(10) Patent No.: US 7,964,217 B2
(45) Date of Patent: *Jun. 21, 2011

(54) DEGRADABLE POLY(ETHYLENE GLYCOL) HYDROGELS WITH CONTROLLED HALF-LIFE AND PRECURSORS THEREFOR

(75) Inventor: J. Milton Harris, Huntsville, AL (US)

(73) Assignee: Nektar Therapeutics, San Carlos, CA (US)

( * ) Notice: Subject to any disclaimer, the term of this patent is extended or adjusted under 35 U.S.C. 154(b) by 166 days.

This patent is subject to a terminal disclaimer.

(21) Appl. No.: 10/684,893

(22) Filed: Oct. 14, 2003

(65) Prior Publication Data

US 2004/0076602 A1 Apr. 22, 2004

Related U.S. Application Data

(63) Continuation of application No. 08/928,049, filed on Sep. 12, 1997, now abandoned.

(60) Provisional application No. 60/026,066, filed on Sep. 13, 1996.

(51) Int. Cl.
*A61K 9/14* (2006.01)
*A61K 31/74* (2006.01)
*A61K 31/765* (2006.01)
*B29B 17/00* (2006.01)
*C08C 2/06* (2006.01)

(52) U.S. Cl. .................. 424/486; 424/78.31; 424/78.37; 528/494; 528/496

(58) Field of Classification Search .............. 514/772.7; 424/486, 78.31, 78.37; 525/403; 528/494, 528/496
See application file for complete search history.

(56) References Cited

U.S. PATENT DOCUMENTS

| | | | |
|---|---|---|---|
| 3,419,006 A | 12/1968 | King | |
| 3,963,805 A | 6/1976 | Chu | |
| 4,179,337 A | 12/1979 | Davis et al. | |
| 4,424,311 A | 1/1984 | Nagaoka et al. | |
| 4,670,417 A | 6/1987 | Iwasaki et al. | |
| 4,894,238 A | 1/1990 | Embry et al. | |
| 5,192,743 A | 3/1993 | Hsu | |
| 5,410,016 A | 4/1995 | Hubbell et al. | |
| 5,550,178 A | 8/1996 | Desai et al. | |
| 5,567,422 A | 10/1996 | Greenwald | |
| 5,571,844 A | 11/1996 | Stüber | |
| 5,573,934 A | 11/1996 | Hubbell et al. | |
| 5,607,687 A | 3/1997 | Bezwada et al. | |
| 5,610,241 A | 3/1997 | Lee et al. | |
| 5,618,528 A | 4/1997 | Cooper et al. | |
| 5,626,863 A | 5/1997 | Hubbell et al. | |
| 5,648,088 A * | 7/1997 | Bezwada et al. ............ 424/426 |
| 5,648,506 A | 7/1997 | Desai et al. | |
| 5,698,213 A * | 12/1997 | Jamiolkowski et al. ...... 424/426 |
| 5,730,968 A | 3/1998 | Butterfield et al. | |
| 5,874,500 A | 2/1999 | Rhee et al. | |

| | | | |
|---|---|---|---|
| 6,051,648 A | 4/2000 | Rhee et al. | |
| 6,166,130 A | 12/2000 | Rhee et al. | |
| 6,214,966 B1 | 4/2001 | Harris | |
| 6,258,351 B1 | 7/2001 | Harris | |
| 6,323,278 B2 | 11/2001 | Rhee et al. | |
| 6,348,558 B1 | 2/2002 | Harris et al. | |
| 6,362,276 B1 | 3/2002 | Harris et al. | |
| 6,432,397 B1 | 8/2002 | Harris | |
| 6,515,100 B2 | 2/2003 | Harris | |
| 6,558,658 B2 | 5/2003 | Harris | |
| 2002/0013408 A1 | 1/2002 | Rhee et al. | |

FOREIGN PATENT DOCUMENTS

| | | |
|---|---|---|
| EP | 0 473 268 A2 | 3/1992 |
| EP | 0 593 284 A1 | 4/1994 |
| EP | 0 771 832 A2 | 5/1997 |
| EP | 0 794 211 A2 | 9/1997 |
| EP | 0 841 360 A1 | 5/1998 |
| WO | WO 92/00748 A1 | 1/1992 |
| WO | WO 93/24476 A1 | 12/1993 |
| WO | WO 94/03155 | 2/1994 |
| WO | WO 95/35093 | 12/1995 |
| WO | WO 96/20012 A2 | 7/1996 |
| WO | WO 97/22371 | 6/1997 |

OTHER PUBLICATIONS

The Aldrich Catalog, http://www.sigmaaldrich.com/etc/medialib/docs/Aldrich/General_Information/glossary.Par.0001.File.tmp/glossary.pdf, obtained online on Jan. 11, 2009.*
J.M. Harris, Ed., "Biomedical and Biotechnical Applications of Poly(Ethylene Glycol) Chemistry", Plenum, New York, 1992.
Greenwald et al., "Highly Water Soluble Taxol Derivatives: 7-Polyethylene Glycol Carbamates and Carbonates", *J. Org. Chem.*, vol. 60, No. 2, pp. 331-336, 1995.
Sawhney et al., "Biorodible Hydrogels Based on Photopolymerized Poly(Ethylene Glycol)-co-pol(α-hydroxy acid), Diacrylate Macromers", *Macromolecules*, vol. 26, No. 4, pp. 581-587 (1993).
Gayet et al., "High Water Content BSA-PEG Hydrogel for Controlled Release Device: Evaluation of the Drug Release Properties", *Journal of Controlled Release 38*, pp. 177-184 (1996).

(Continued)

*Primary Examiner* — Johann R Richter
*Assistant Examiner* — Abigail Fisher
(74) *Attorney, Agent, or Firm* — Alston & Bird LLP

(57) ABSTRACT

This invention relates to hydrolytically degradable gels of crosslinked poly(ethylene) glycol (PEG) structures. Addition of water causes these crosslinked structures to swell and become hydrogels. The hydrogels can be prepared by reacting two different PEG derivatives containing functional moieties at the chain ends that react with each other to form new covalent linkages between polymer chains. The PEG derivatives are chosen to provide covalent linkages within the crosslinked structure that are hydrolytically degradable. Hydrolytic degradation can provide for dissolution of the gel components and for controlled release of trapped molecules, including drugs. Reagents other than PEG can be avoided. The hydrolysis rates can be controlled by varying atoms adjacent to the hydrolytically degradable functional groups to provide substantially precise control for drug delivery in vivo.

21 Claims, 1 Drawing Sheet

OTHER PUBLICATIONS

Jeong et al., "Biodegradable Block Copolymers As Injectable Drug-Delivery Systems", *Nature*, 1997, pp. 860-862, vol. 388, No. 28.

Martinez et al, "Branched Poly(Ethylene Glycol) Linkers", *Macromolecular Chemistry And Physics*, 1997, pp. 2489-2498, vol. 198, No. 8.

Pitt et al, "Manipulation Of The Rate Of Hydrolysis Of Polymer-Drug Conjugates: The Secondary Structure Of The Polymer", *Journal Of Controlled Release*, 1996, pp. 221-229, vol. 39, No. 2.

Zalipsky, "Functionalized Poly(ethylene glycol) for Preparation of Biologically Relevant Conjugates", *Bioconjugate Chem.*, 1995, pp. 150-165, vol. 6, No. 2.

Yang et al., "Activity and Stability of Enzymes Incorporated into Acrylic Polymers", *J. Am. Chem. Soc.*, 1995, pp. 4843-4850, vol. 117, No. 17.

\* cited by examiner

Figure 1. Sketch of PEG hydrogels
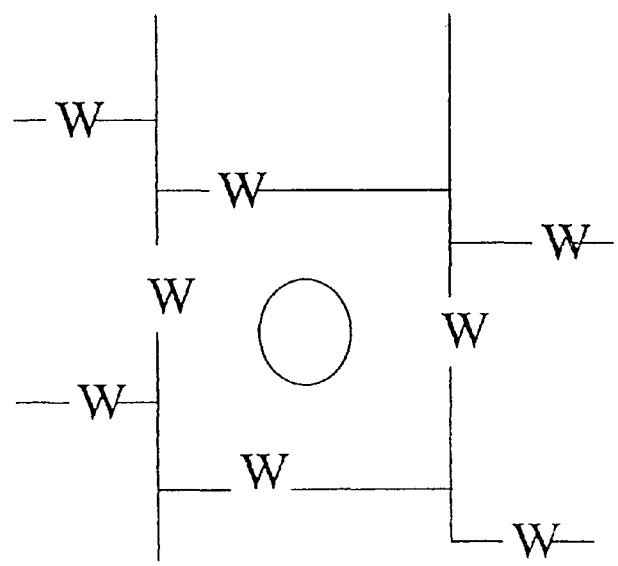

DEGRADABLE POLY(ETHYLENE GLYCOL) HYDROGELS WITH CONTROLLED HALF-LIFE AND PRECURSORS THEREFOR

CROSS REFERENCE TO RELATED APPLICATION

This application is a continuation application of application Ser. No. 08/928,049, filed Sep. 12, 1997 now abandoned, which is related to commonly owned copending Provisional Application Ser. No. 60/026,066, filed Sep. 13, 1996, and claims the benefit of its earlier filing date under 35 U.S.C. 119(e).

FIELD OF THE INVENTION

This invention relates to poly(ethylene glycol) hydrogels, precursors therefor, methods for making the precursors and hydrogels, and the use of the precursors and hydrogels.

BACKGROUND OF THE INVENTION

In its most common form, poly(ethylene glycol) (PEG) is a linear polymer terminated at each end with hydroxyl groups:

$$HO—CH_2CH_2O—(CH_2CH_2O)_n—CH_2CH_2—OH$$

This polymer can be represented in brief form as HO-PEG-OH where it is understood that -PEG- represents the following structural unit:

$$—CH_2CH_2O—(CH_2CH_2O)_n—CH_2CH_2—$$

n typically ranges from approximately 10 to 2000.

PEG is of great utility in biotechnology and is useful in a variety of applications for drug delivery and modification of surfaces to promote nonfouling characteristics, including as hydrogels and for covalent attachment to various drugs and surfaces. PEG is not toxic, does not tend to promote an immune response, and is soluble in water and in many organic solvents.

The PEG polymer can be covalently attached to insoluble molecules to make the resulting PEG-molecule conjugate soluble. For example, Greenwald, Pendri and Bolikal in *J. Org. Chem.,* 60, 331-336 (1995) recite that the water-insoluble drug taxol, when coupled to PEG, becomes water soluble.

Davis et al. in U.S. Pat. No. 4,179,337 recite that proteins coupled to PEG have an enhanced blood circulation lifetime because of a reduced rate of kidney clearance and reduced immunogenicity. The lack of toxicity of the polymer and its rate of clearance from the body are important considerations in pharmaceutical applications. Pharmaceutical applications and many leading references are described in the book by Harris (J. M. Harris, Ed., "Biomedical and Biotechnical Applications of Polyethylene Glycol Chemistry," Plenum, New York, 1992).

PEG is commonly used as methoxy-PEG-OH, or mPEG in brief, in which one terminus is the relatively inert methoxy group, while the other terminus is an hydroxyl group that is subject to ready chemical modification.

$$CH_3O—(CH_2CH_2O)_n—CH_2CH_2—OH \quad mPEG$$

PEG is also commonly used in branched forms that can be prepared by addition of ethylene oxide to various polyols, including glycerol, pentaerythritol and sorbitol. For example, the four-armed branched PEG prepared from pentaerythritol is shown below:

$$C(CH_2—OH)_4+nC_2H_4O \rightarrow C[CH_2O—(CH_2CH_2O)_n—CH_2CH_2—OH]_4$$

The branched PEGs can be represented in general form as $R(\text{-PEG-OH})_n$ in which R represents the central core molecule, which can include glycerol or pentaerythritol, and n represents the number of arms.

It is necessary to use an "activated derivative" of PEG to couple PEG to a molecule. The hydroxyl group located at the PEG terminus or other group subject to ready chemical modification is activated by modifying or replacing the group with a functional group suitable for reacting with a group on another molecule, including proteins, surfaces, enzymes, and others. For example, the succinimidyl "active ester" of carboxymethylated PEG forms covalent bonds with amino groups on proteins as described by K. Iwasaki and Y. Iwashita in U.S. Pat. No. 4,670,417.

The synthesis described in U.S. Pat. No. 4,670,417 is illustrated below with the active ester reacting with amino groups of a protein in which the succinimidyl group is represented as NHS and the protein is represented as $PRO—NH_2$:

$$PEG\text{-}O—CH_2—CO_2—NHS+PRO—NH_2 \rightarrow PEG\text{-}O—CH_2—CO_2—NH—PRO$$

Succinimidyl "active esters", such as $PEG\text{-}O—CH_2—CO_2—NHS$, are commonly used forms of activated carboxylic acid PEGs, and they are prepared by reacting carboxylic acid PEGs with N-hydroxylsuccinimide.

Problems have arisen in the art. Some of the functional groups that have been used to activate PEG can result in toxic or otherwise undesirable residues when used for in vivo drug delivery. Some of the linkages that have been devised to attach functional groups to PEG can result in an undesirable immune response. Some of the functional groups do not have sufficient or otherwise appropriate selectivity for reacting with particular groups on proteins and can tend to deactivate the proteins.

PEG hydrogels, which are water-swollen gels, have been used for wound covering and drug delivery. PEG hydrogels are prepared by incorporating the soluble, hydrophilic polymer into a chemically crosslinked network or matrix so that addition of water produces an insoluble, swollen gel. Substances useful as drugs typically are not covalently attached to the PEG hydrogel for in vivo delivery. Instead, the substances are trapped within the crosslinked matrix and pass through the interstices in the matrix. The insoluble matrix can remain in the body indefinitely and control of the release of the drug typically can be somewhat imprecise.

One approach to preparation of these hydrogels is described by Embrey and Grant in U.S. Pat. No. 4,894,238. The ends of the linear polymer are connected by various strong, nondegradable chemical linkages. For example, linear PEG is incorporated into a crosslinked network by reacting with a triol and a diisocyanate to form hydrolytically stable urethane linkages that are nondegradable in water.

A related approach for preparation of PEG hydrogels has been described by Gayet and Fortier in *J. Controlled Release*, 38, 177-184 (1996) in which linear PEG was activated as the p-nitrophenylcarbonate and crosslinked by reaction with a protein, bovine serum albumin. The linkages formed are hydrolytically stable urethane groups and the hydrogels are nondegradable in water.

In another approach, described by N. S. Chu in U.S. Pat. No. 3,963,805, nondegradable PEG networks have been prepared by random entanglement of PEG chains with other polymers formed by use of free radical initiators mixed with multifunctional monomers. P. A. King described nondegradable PEG hydrogels in U.S. Pat. No. 3,149,006 that have been prepared by radiation-induced crosslinking of high molecular weight PEG.

Nagaoka et al. in U.S. Pat. No. 4,424,311 have prepared PEG hydrogels by copolymerization of PEG methacrylate with other comonomers such as methyl methacrylate. Substantial non-PEG polymeric elements are introduced by this method. Vinyl polymerization produces a polyethylene backbone with PEG attached. The methyl methacrylate comonomer is added to give the gel additional physical strength.

Sawhney, Pathak and Hubbell in *Macromolecules*, 26, 581 (1993) describe the preparation of block copolymers of polyglycolide or polylactide and PEG that are terminated with acrylate groups, as shown below.

$$CH_2=CH-CO-(O-CH_2-CO)_n-O-PEG-O-(CO-CH_2-O)_n-CO-CH=CH_2$$

In the above formula, the glycolide blocks are the —O—CH$_2$—CO— units; addition of a methyl group to the methylene gives a lactide block; n can be multiples of 2. Vinyl polymerization of the acrylate groups produces an insoluble, crosslinked gel with a polyethylene backbone.

Substantial non-PEG elements are introduced into the hydrogel. The polylactide or polyglycolide segments of the polymer backbone shown above, which are ester groups, are susceptible to slow hydrolytic breakdown, with the result that the crosslinked gel undergoes slow degradation and dissolution.

Non-PEG elements tend to introduce complexity into the hydrogel and degradation and dissolution of the matrix can result in undesirable or toxic components being released into the blood stream when the hydrogels are used in vivo for drug delivery.

It would be desirable to provide alternative PEG hydrogels that are suitable for drug delivery and that have unique properties that could enhance drug delivery systems.

SUMMARY OF THE INVENTION

The invention provides chemically crosslinked degradable PEG hydrogels capable of controlled degradability and methods for making these PEG hydrogels in the absence of substantial non-PEG elements. Weak chemical linkages are introduced into the hydrogel that provide for hydrolytic breakdown of the crosslinks and release of drug molecules that can be trapped within the matrix. The gels break down to substantially nontoxic PEG fragments that typically are cleared from the body. Variation of the atoms near the hydrolytically unstable linkages can provide precise control of hydrolytic breakdown rate and drug release.

Examples of hydrolytically unstable linkages include carboxylate ester, phosphate ester, acetals, imines, orthoesters, peptides and oligonucleotides. These weak links are formed by reaction of two PEGs having different terminal groups as illustrated below:

-PEG-Z+Y-PEG- → -PEG-W-PEG-

In the above illustration, —W— represents the hydrolytically unstable weak link. Z— and Y— represent groups located at the terminus of the PEG molecule that are capable of reacting with each other to form weak links —W—.

For example, the following pairs of Z and Y groups can be used to form some of the W groups described above:

| | |
|---|---|
| -PEG-CO$_2$H + HO-PEG- → -PEG-CO$_2$-PEG- | ester |
| -PEG-OPO$_3$H$_2$ + HO-PEG → -PEG-OPO$_3$(H)-PEG- | phosphate ester |
| -PEG-CHO + (HO-PEG)$_2$- → -PEG-CH(O-PEG)$_2$- | acetal |
| -PEG-CHO + NH$_2$-PEG- → -PEG-CH=N-PEG- | imine |

The PEG hydrogels of the invention can be made by either a two-step or a one-step method. In the one-step approach, two different PEGs with the appropriate terminal groups are reacted in a single step. A specific example of the one-step approach according to the invention is shown in the following equation for coupling of linear PEG acids with a three-armed PEG terminated with hydroxyl groups. Weak ester linkages are formed.

$$HO_2C-(CH_2)_n-O-PEG-O-(CH_2)_n-CO_2H+CH_3C(CH_2-O-PEG-OH)_3 \rightarrow \{CH_3C[CH_2-O-PEG-O_2C-(CH_2)_n-O-PEG-O(CH_2)_n-CO_2-]_3\}_m-H_2O$$

The degree of polymerization is given by m, which refers to "matrix" and is intended to indicate that a crosslinked polymer has been formed as a solid aggregate. It should be understood that the degree of polymerization by the formation of crosslinks is large and indeterminate. The PEG hydrogel that is formed is a visible and solid aggregate that swells in water in which, in theory, all available crosslinks are formed. However, it is not usually possible to determine the degree of crosslinking that has occurred.

The rate of release of drug molecules trapped within the matrix is controlled by controlling the hydrolytic breakdown rate of the gel. The hydrolytic breakdown rate of the gel can be adjusted by controlling the degree of bonding of the PEGs that form the hydrogel matrix. A multiarmed PEG having 10 branches or arms will break down and release drug molecules more slowly than a 3 armed PEG.

Substantially precise control of hydrolytic breakdown rate and drug release can be provided by varying the atoms near the hydrolytically unstable linkages. Typically, increasing the n value (the number of methylene groups) in the above structure decreases the hydrolysis rate of esters and increases the time required for the gel to degrade. If n in the above example is 1, then the ester linkages of the gel will hydrolyze with a half life of about 4 days at pH 7 and 37° C. If n is 2, then the half life of hydrolytic degradation of the ester linkages is about 43 days at pH 7 and 37° C.

Phosphate esters, acetals, imines, and other hydrolytically unstable linkages can be similarly formed and the hydrolysis rate can be similarly controlled by controlling the number of methylene groups adjacent the hydrolytically unstable linkage and by controlling the degree of branching of the PEG.

The degradable hydrogels of this invention can also be made by a two-step process. In the first step, soluble, uncrosslinked PEGs are prepared that have hydrolytically unstable linkages in their backbones. In the second step, these PEGs with hydrolytically unstable linkages in their backbones are coupled together with other PEGs by hydrolytically stable linkages. For example, the following PEG has two hydrolytically unstable ester linkages in its backbone:

$$NHS-O_2C-CH_2-O-PEG-O-CH_2-CO_2-PEG-O_2C-CH_2-O-PEG-O-CH_2-CO_2-NHS$$

The above PEG is activated at each terminus with an N-hydroxylsuccinimide moiety (NHS) in which the active succinimidyl ester moiety is NHS—CO$_2$— and is reactive with amino groups. When this PEG is coupled with a multiarmed PEG amine, a crosslinked network is produced that is held together by stable amide linkages that are formed from the reaction of the active esters with amine and by the hydrolytically unstable ester linkages already present in the backbone. As in the previous example, the degradation rate of the gel is controlled by varying the number of methylene groups adjacent to the ester linkage.

The two-step method described above for making the PEG hydrogels can be used to form the gel and to trap substances in situ, in living tissue, for injectable drug systems. A drug can be combined with one reactive PEG component of the hydrogel and injected along with another reactive PEG component that will form the gel. The drug is trapped within the matrix that is formed because of its proximity to the reactive system.

Thus, the invention provides, among other things, degradable PEG hydrogels having hydrolytically unstable linkages in which the rate of hydrolysis of the unstable linkages can be controlled. The PEG hydrogels of the invention can physically trap drugs, including proteins, enzymes, and a variety of other substances, in the absence of covalent linkages, for precisely controlled release in vivo. The degraded gel can be more readily cleared from the body than can gels that do not significantly degrade.

The foregoing and other objects, advantages, and features of the invention, and the manner in which the same are accomplished, will be more readily apparent upon consideration of the following detailed description of the invention taken in conjunction with the accompanying drawing, which illustrates an exemplary embodiment.

BRIEF DESCRIPTION OF THE DRAWINGS

FIG. 1 is a schematic representation of a PEG hydrogel in which the PEGs have three branches or arms.

DETAILED DESCRIPTION

FIG. 1 illustrates a poly(ethylene glycol) (PEG) matrix held together by hydrolytically unstable or weak linkages W. The PEGs shown in FIG. 1 have three branches or arms. The degree of branching can be varied in the hydrogels of the invention to control the physical strength and compressibility of the gels; in general the greater the degree of branching and the shorter the branches, the greater the strength (resistance to compression or stretching) of the gels. Similarly, greater degrees of branching and shorter branches also give smaller pores and lower water content.

Degradable PEG hydrogels having hydrolytically unstable PEGs can be prepared in one step, as shown in the following general equation:

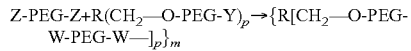

where m means "matrix" and indicates a degree of polymerization such that a crosslinked polymer, which is a solid aggregate is formed. m is large and indeterminate. p is 3 to 10 and refers to the degree of branching, which is the number of arms, of the reactant branched PEG, $R(CH_2-O-PEG-Y)_p$. The rate of hydrolysis of the PEG gel typically is lengthened by increasing p. R is a central branching moiety suitable for making multiarmed PEGs and includes moieties selected from the group consisting of glycerol, glycerol oligomers, pentaerythritol, sorbitol, trimethyolpropane, and di(trimethyolpropane). Z and Y are groups that react to form hydrolytically unstable linkages W. Examples of pairs of the groups Z and Y that can be reacted to form hydrolytically unstable linkages W include pairs selected from the group consisting of alcohol and carboxylic acid reacting to form carboxylate esters, amine and aldehyde reacting to form imines, hydrazide and aldehyde reacting to form hydrazones, alcohol and phosphate reacting to form phosphate ester, aldehyde and alcohol reacting to form acetals, alcohols and formate reacting to form orthoesters, peptides formed by reaction of PEG amine with PEG-peptide terminated with carboxyl to form a new peptide linkage, peptides formed by reaction of PEG carboxylic acid with PEG-peptide terminated with amine to form a new peptide linkage, and oligonucleotides formed by reaction of PEG phosphoramidite with an 5'-hydroxyl-terminated PEG oligonucleotide.

It should be noted that the Z groups are shown on a linear PEG and the Y groups are shown on a branched PEG. However, the reaction will proceed and the gel will be formed with the Y groups on the linear PEG and the Z groups on the branched PEG to form the same weak linkages W.

A specific example of the one-step method for making a PEG hydrogel having hydrolytically unstable carboxylate ester linkages W formed by the reaction of PEG carboxylic acid and PEG hydroxyl groups Z and Y, respectively, is shown by the following equation:

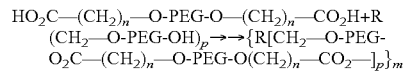

In the above equation, m, p, and R are as characterized above. n is from about 1 to 10, and can be varied to control the rate of hydrolysis of the gel. Increasing n typically decreases the rate of hydrolysis.

Note that in this example the hydroxyl group is on the branched PEG while the carboxylic acid groups are on the linear PEG. Alternatively, the hydroxyl group could be on the linear PEG while the carboxylic acid could be on the branched PEG.

Degradable PEG hydrogels can also be prepared in two steps. In the first step a linear PEG is prepared having one or more hydrolytically unstable linkages W in its backbone. The linear PEG has the general formula U-PEG-W-PEG-U, in which U represents a reactive terminal moiety and W is the hydrolytically unstable linkage.

In the second step the PEG with the hydrolytically unstable linkages in its backbone is reacted with a second PEG. The second PEG is a branched PEG, as shown in the general formula $R(CH_2-O-PEG-V)_p$, in which V represents a reactive terminal moiety. P is 3 to 10 and refers to the degree of branching, which is the number of arms, of the reactant branched PEG, $R(CH_2-O-PEG-V)_p$. The rate of hydrolysis of the PEG gel typically is lengthened by increasing p. R is a central branching moiety suitable for making multiarmed PEGs and includes moieties selected from the group consisting of glycerol, glycerol oligomers, pentaerythritol, sorbitol, trimethyolpropane, and di(trimethyolpropane).

The functional groups U and V at the ends of the PEG polymer chains in the first and second PEGs, respectively, react to form hydrolytically stable crosslinks X, as shown by the following equation.

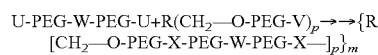

Again, m means "matrix" and indicates a degree of polymerization such that a crosslinked polymer, which is a solid aggregate is formed. W is a hydrolytically unstable group including carboxylate esters, imines, phosphate esters, acetals, orthoesters, peptides, and oligonucleotides. U and V are groups reactive toward each other, including active esters, which includes carbonate esters, reacting with amines, isocyanates reacting with alcohols, isocyanates reacting with amines, aldehydes reacting with amines and a reducing agent, epoxide reacting with amines, and sulfonate esters reacting with amines.

The hydrolytically stable linkages X that are formed by the reaction of U and V include amide from the reaction of active esters with amine, urethane from the reaction of isocyanate with alcohol, urea from the reaction of isocyanate with amine, amine from the reaction of aldehyde with amine and reducing agent, amine from the reaction of epoxide with amine, and sulfonamide from the reaction of sulfonate ester with amine.

A specific example of the two-step method is the preparation of degradable PEG hydrogels having hydrolytically unstable carboxylate ester linkages W and hydrolytically stable amide linkages X that are formed by the reaction of active esters U and amines V as shown in the following equation.

$$NHS—O_2C—(CH_2)_n—O\text{-PEG-}W\text{-PEG-}O—(CH_2)_n—CO_2—NHS+R(CH_2—O\text{-PEG-}NH_2)_p \rightarrow \{R[CH_2—O\text{-PEG-}NHCO—(CH_2)_n—O\text{-PEG-}W\text{-PEG-}O—(CH_2)_n—CONH—]_p\}_m$$

The symbols n, m, p, and R are as previously described. W is a hydrolytically unstable ester linkage according to the formula —O—$(CH_2)_r$—$CO_2$— in which r is from about 1 to 10.

The amino group V is on the branched PEG while the active esters U are on the linear PEG. It should be recognized that the two groups could be exchanged so that the amino group is presented on the linear PEG while the active ester is presented on the branched PEG.

In a second two-step method, a reactant linear PEG is prepared in a first step having hydrolytically unstable linkages W near the polymer chain terminal groups U—R'. In a second step the PEG having hydrolytically unstable linkages W near the polymer chain terminal groups is reacted with a branched PEG having a reactive moiety V to form hydrolytically stable crosslinks X.

$$U—R'—W\text{-PEG-}W—R'—U+R(CH_2—O\text{-PEG-}V)_p \rightarrow \{R[CH_2—O\text{-PEG-}X—R'—W\text{-PEG-}W—R'—X]_p\}_m$$

The symbols m, p, and R are as previously defined. R' is a small hydrocarbon fragment having from about 1 to 10 carbons. W is a hydrolytically unstable group including carboxylate esters, imines, phosphate esters, acetals, orthoesters, peptides, and oligonucleotides, as previously defined. U and V are groups reactive toward each other, including active esters, which includes carbonate esters, reacting with amines, isocyanates reacting with alcohols, isocyanates reacting with amines, aldehydes reacting with amines and a reducing agent, epoxides reacting with amines, and sulfonate esters reacting with amines.

The hydrolytically stable linkage formed by reaction of U and V is X. X includes amide from the reaction of active ester with amine, urethane from the reaction of carbonate ester with amine, urethane from the reaction of isocyanate with alcohol, urea from the reaction of isocyanate with amine, amine from the reaction of aldehyde with amine and reducing agent, amine from the reaction of epoxide with amine, and sulfonamide from the reaction of sulfonate ester with amine.

A specific example, which is shown in the following equation, is the formation of PEG hydrogels containing hydrolytically unstable carboxylate ester groups W and hydrolytically stable amides X formed by the reaction of active esters U and amines V, and in which the hydrolytically unstable carboxylate ester groups W have been separated from the U and or V groups by a small hydrocarbon fragment in the precursor linear PEG.

$$NHS—O_2C—(CH_2)_i—O_2C—(CH_2)_n—O\text{-PEG-}O—(CH_2)_n—CO_2—(CH_2)_i—CO_2—NHS+R(CH_2—O\text{-PEG-}NH_2)_p \rightarrow \{R[CH_2—O\text{-PEG-}NHCO—(CH_2)_i—O_2C—(CH_2)_n—O\text{-PEG-}O—(CH_2)_n—CO_2—(CH_2)_n—CONH—]_p\}_m$$

In the above equation, i is from about 1 to 10 and defines the length of the small hydrocarbon fragment R'. The symbols n, m, p and R are as previously defined. An amino group is shown on the branched PEG while the active esters are shown on the linear PEG. It should be recognized that the two groups could be exchanged so that the amino group is on the linear PEG and the active ester is on the branched PEG.

The skilled artisan should recognize that when reference is made to a Z moiety reacting with a Y moiety or to a U moiety reacting with a V moiety, that additional reagents or steps may be employed according to commonly accepted chemical procedures and standards to achieve the desired linkage W or X as the case may be. There are many possible routes, too numerous to mention here, that could be taken and that should be readily apparent to the skilled artisan. For example, one of skill in the art can be expected to understand that when an alcohol and a carboxylic acid are reacted, the acid typically is converted to another form, the acid chloride, prior to reaction with alcohol. Several examples are demonstrated in the Examples below.

Hydrogels made from the crosslinked PEG polymeric structures of the invention can be used in drug delivery systems and for wound dressings. Wound dressings could be used internally to provide dressings that degrade within the body over time. The hydrogels of the invention could be usefully applied in drug delivery systems to burns to apply therapeutic agents to burns. Drug delivery systems can be prepared in which the rate of hydrolysis of the hydrogel is controlled to provide controlled release of drug components. By "drug" is meant any substance intended for the diagnosis, cure, mitigation, treatment, or prevention of disease in humans and other animals, or to otherwise enhance physical or mental well being. The invention could be used for delivery of biologically active substances generally that have some activity or function in a living organism or in a substance taken from a living organism.

The terms "group," "functional group," "moiety," "active moiety," "reactive site," and "radical" are all somewhat synonymous in the chemical arts and are used in the art and herein to refer to distinct, definable portions or units of a molecule and to units that perform some function or activity and are reactive with other molecules or portions of molecules.

The term "linkage" is used to refer to groups that normally are formed as the result of a chemical reaction and typically are covalent linkages. Hydrolytically stable linkages means that the linkages are stable in water and do not react with water at useful pHs for an extended period of time, potentially indefinitely. Hydrolytically unstable linkages are those that react with water, typically causing degradation of a hydrogel and release of substances trapped within the matrix. The linkage is said to be subject to hydrolysis and to be hydrolyzable. The time it takes to degrade the crosslinked polymeric structure is referred to as the rate of hydrolysis and is usually measured in terms of its half life.

The skilled artisan should recognize that when reference is made to a Z moiety reacting with a Y moiety or to a U moiety reacting with a V moiety, that additional reagents or steps may be employed according to commonly accepted chemical procedures and standards to achieve the desired linkage W or X as the case may be. There are many possible routes, too numerous to mention here, that could be taken and that should be readily apparent to the skilled artisan. For example, one of skill in the art can be expected to understand that when an alcohol and a carboxylic acid are reacted, the acid typically is converted to another form, the acid chloride, prior to reaction with alcohol. Several examples are demonstrated in the Examples below.

The following examples show the synthesis of various examples of the invention.

EXAMPLES

Example 1

Example 1 shows preparation of a degradable PEG hydrogel having a hydrolytically unstable ester linkage. In an aluminum pan of 1 inch diameter, difunctional PEG 2000 acid (600 mg, 0.6 mmole end groups, available from Shearwater Polymers in Huntsville, Ala.) and one equivalent of 8-arm PEG 10,000 (750 mg, Shearwater Polymers) were mixed with 30 mg stannous 2-ethylhexanoate (Sigma Chemical) and melted. PEG acids used included PEG carboxymethyl acid (-PEG-OCH$_2$COOH), PEG propionic acid (-PEG-O—CH$_2$CH$_2$COOH), and PEG succinic acid (-PEG-OOCCH$_2$CH$_2$COOH). After a thin film of the melt covered the pan surface uniformly, the pan was heated under vacuum at 130° C. and 100 millitorr for 6-24 hours. A firm, transparent gel formed. After cooling in a N$_2$ stream, the gel became translucent and was cut into thin disks and purified by the following procedures.

The crude gels were swollen in glacial acetic acid and washed three times with this solvent during a 2-3 days period. For hydrogels with a low swelling degree, swelling was conducted in dioxane before the wash with glacial acetic acid to avoid breaking of highly crosslinked gels. After washing, the gels were dried under vacuum. The tin content of the gel was determined by inductively coupled plasma spectroscopy to be less than 60 ppm.

Example 2

Example 2 shows preparation of a degradable PEG hydrogel having a hydrolytically unstable imine linkage. In a test tube, difunctional PEG propionic aldehyde 3400 (100 mg, 58.8 μmole, Shearwater Polymers) and 8-arm PEG amine 10,000 (74 mg, 58.8 μmole) were dissolved in 1,4-dioxane (Aldrich Chemical). The test tube was heated on an oil bath at 70° C. for about two hours. The gel was then dried under reduced pressure at room temperature.

The PEG aldehydes used included PEG propionaldehyde (-PEG-OCH$_2$CH$_2$CHO), PEG acetaldehyde (-PEG-OCH$_2$CHO), and PEG benzaldehyde (-PEG-O—C$_6$H$_4$—CHO).

Examples 3 and 4, below, show preparation of PEG derivatives having hydrolytically unstable linkages for use in preparing the degradable hydrogel of the invention.

Example 3

Example 3 shows synthesis of PEG derivatives having hydrolytically unstable backbone linkages and NHS active carbonates at each terminus thereof. The PEG derivative can be represented as NHS—OOCO-PEG-W-PEG-OCOO—NHS where W represents the hydrolytically unstable linkage. In a 100 ml round-bottom flask, benzyloxy-PEG carboxymethyl acid 3400 (3.4 g, 1 mmol, Shearwater Polymers) in toluene was azeotropically distilled for two hours and then cooled to room temperature. A solution of thionyl chloride (2M, 4 ml, 8 mmole, Aldrich) in methylene chloride was injected and the mixture was stirred under N$_2$ overnight. The solvent was condensed by rotary evaporation and the syrup was dried in vacuo for about four hours over P$_2$O$_5$ powder. To the residue was added anhydrous methylene chloride (5 ml) and azeotropically dried benzyloxy-PEG 3400 (2.55 g, 0.75 mmol) in toluene (20 ml). After the benzyloxy-PEG acyl chloride was dissolved, freshly distilled triethylamine (0.6 ml) was added. The mixture was stirred overnight, the triethylamine salt filtered off, and the product collected by precipitation with ethyl ether. It was further purified by dissolving in water and extracting with methylene chloride. The organic phase was dried over anhydrous sodium sulfate, condensed under vacuum, and precipitated into ethyl ether. The precipitate was dried in vacuo. HPLC (GPC) of the product showed that 100% of benzyloxy-PEG had been converted into the PEG ester and about 15% wt % benzyloxy-PEG acid remained.

The mixture was chromatographically purified on an ion-exchange column (DEAE sepharose fast flow, Pharmacia) to remove the benzyloxy-PEG acid. 100% pure α-benzyloxy-ω-benzyloxy PEG ester 6800 was obtained. Yield: 4.1 gram (80%).

A solution of α-benzyloxy-ω-benzyloxy PEG ester 6800 (2 g, 0.59 mmole) in 1,4-dioxane (20 ml) was hydrogenolyzed with H$_2$ (2 atm pressure) and Pd/C (1 g, 10% Pd) overnight. The catalyst was removed by filtration and the product precipitated into ethyl ether after most of the solvent was removed on a rotary evaporator. α-hydroxy-ω-hydroxy PEG ester 6800 was collected by filtration and dried in vacuo. Yield: 1.5 gram (75%).

α-hydroxy-ω-hydroxy PEG ester 6800 (1.5 g, 0.44 mmole end group) was azeotropically dried with 100 ml acetonitrile and cooled to room temperature. To this solution was added disuccimidyl carbonate (DSC) (0.88 mmole, Fluka) and pyridine (0.1 ml), and the solution was stirred at room temperature overnight. The solvent was removed under vacuum and the syrup was dried in vacuo. The product was dissolved in 35 ml of dry methylene chloride, the insoluble solid was removed by filtration, and the filtrate washed with pH 4.5 sodium chloride saturated acetate buffer. The organic phase was dried over anhydrous sodium sulfate, condensed under vacuum, and precipitated into ethyl ether. The precipitate was dried over P$_2$O$_5$ in vacuo. Yield: 1.4 g (93%). NMR (DMSO-d$_6$): (1) product from benzyloxy-PEG propionic acid: δ 3.5 (br m, PEG), 2.55 (t, —OCH$_2$CH$_2$COOPEG-), 4.13 (t, -PEG-COOCH$_2$CH$_2$O—), 4.45 (t, -$\overline{\text{PEG}}$OCH$_2$CH$_2$OCO—NHS), 2.80 (s, $\overline{\text{NHS}}$, 4H); (2) product from ben$\overline{\text{zy}}$loxy-PEG carboxymethyl acid: δ 3.5 (br m, PEG), 4.14 (s, —OCH$_2$COOPEG-), 4.18 (t, —OCH$_2$COOCH$_2$CH$_2$—), $\overline{4.45}$ (t, -PEGO—CH$_2$CH$_2$OCONHS), 2.81 [s, N$\overline{\text{HS}}$, 4H].

Example 4

Example 4 shows synthesis of PEG derivatives having hydrolytically unstable backbone linkages and terminal NHS active esters. The PEG derivative can be represented by the formula NHS—OOC—(CH$_2$)$_n$—O-PEG-W-PEG-O—(CH$_2$)$_n$—COONHS where W is a hydrolytically unstable linkage. In a 100 ml round-bottom flask, α-hydroxy-PEG acid 2000 (4 g, 2 mmol, Shearwater Polymers) and difunctional PEG propionic acid 2000 (4 g, 2 mmole, Shearwater Polymers) were azeotropically distilled with 70 ml toluene under N$_2$. After two hours, the solution was cooled to room temperature and stannous 2-ethylhexanoate (200 mg, Sigma Chemical) was added. The solution was then refluxed under $N_2$ for 24 hours. The solvent was then condensed under vacuum and the syrup precipitated into 100 ml of ether. The product was collected by filtration, dried under vacuum, and dissolved in a sodium acetate buffer solution at pH 5.0. The slightly milky solution was centrifuged and the upper clear solution was extracted three times with methylene chloride. The organic phase was dried over anhydrous sodium sulfate, filtered, condensed under vacuum, and precipitated into ether. The product was collected by filtration and dried under vacuum. Yield 7 g (88%). HPLC: 70% product, 15% di-acid reactant and 15% monoacid. The mixture was further purified by ion exchange chromatography and gel permeation chromatography. $^1$H NMR (DMSO-$d_6$): (1) product from PEG carboxymethyl acid: δ 3.5 (br m, PEG), 4.15 (s, —OC$\underline{H_2}$COOCH$_2$—), 4.18 (t, —OCH$_2$COOC$\underline{H_2}$CH$_2$—); (2) product from PEG propionic acid: δ 3.5 (br $\underline{m}$, PEG), 2.58 (t, —OCH$_2$C$\underline{H_2}$COOCH$_2$—), 4.13 (t, —OCH$_2$CH$_2$COOC$\underline{H_2}$CH$_2$—).

In a round-bottom flask, the difunctional acid having weak linkages (obtained from previous step) (2 g. approx. 1 mmole end group) and N-hydroxysuccinimide (NHS) (126 mg, 1.05 mmole) were dissolved in 50 ml of dry methylene chloride. To this solution was added dicyclohexylcarbodiimide (240 mg, 1.15 mmole) in 5 ml dry methylene chloride. The mixture was stirred under $N_2$ overnight. The solvent was condensed and the syrup was redissolved in 15 ml of anhydrous toluene. The insoluble salt was removed by filtration and the filtrate was precipitated into 200 ml of dry ethyl ether. The precipitate was collected by filtration and dried in vacuo. Yield 1.88 g (94%). $^1$H NMR(DMSO-$d_6$): δ 3.5 (br m, PEG), 2.8 (s, NHS, 4H), 4.6 (s, -PEG-O—C$\underline{H_2}$—COONHS) or 2.85 (t, -PEG-O—CH$_2$C$\underline{H_2}$—COONHS).

Example 5

Example 5 shows preparation of a degradable PEG hydrogel from branched PEG amine and PEG derivatives made in accordance with Example 3 in which the PEG derivatives have hydrolytically unstable backbone linkages and terminal NHS active carbonates, which can be represented as NHS—OOCO-PEG-W-PEG-OCOO—NHS. In a test tube, 100 mg (4.7 μmole) of difunctional PEG active carbonate 6800 (NHS—OOCO-PEG-W-PEG-OCOONHS, prepared in Example 3) was dissolved in 0.75 ml of water, and a buffered solution (0.1M phosphate, pH 7) of 0.15 ml 8-arm-PEG-amine 10,000 (250 mg/ml was added. After rapid shaking, it was allowed to sit and a gel formed in a few minutes. A suitable buffer pH range was found to be 5.5 to 8.

Example 6

Example 6 shows preparation of degradable PEG hydrogels from branched PEG amine and PEG derivatives made in accordance with Example 4 in which the PEG derivatives have hydrolytically unstable backbone linkages and terminal NHS active carbonates that can be represented as NHS—OOC—(CH$_2$)$_n$—O-PEG-W-PEG-O—(CH$_2$)$_n$—COO—NHS. 100 mg (approx. 50 μmole) difunctional PEG active ester (NHS—OOC—(CH$_2$)$_n$—O-PEG-W-PEG-O—(CH$_2$)$_n$—COO—NHS, prepared in Example 4) was dissolved in 0.75 ml of water, and a buffered solution (0.1 M phosphate, pH 7) of 0.25 ml 8-arm-PEG-amine 10,000 (250 mg/ml) was added. After rapid shaking, it was allowed to sit and a gel formed in a few minutes. A suitable buffer pH range was found to be 5.5 to 8.

Example 7

Example shows the synthesis of difunctional PEG-hydroxybutyric acid (HBA), which can be represented as HOOC—CH$_2$—CH(CH$_3$)—OOC—(CH$_2$)$_n$—O-PEG-O—(CH$_2$)$_n$—COOCH(CH$_3$)CH$_2$—COOH for use in preparing the reactive PEGs of Example 8. PEG acid 2000 (2.0 g, 1 mmole, carboxymethyl acid (CM) or propionic acid (PA)) was azeotropically dried with 60 ml toluene under $N_2$. After two hours, the solution was cooled to room temperature and thionyl chloride (3 ml, 6 mmole, in CH$_2$Cl$_2$) was added. The mixture was then stirred at room temperature overnight and the solution condensed by rotary evaporation. The residue was dried in vacuo for about four hours with $P_2O_5$ powder. 3-hydroxybutyric acid (0.30 g, 2.7 mmole) was azeotropically dried with 70 ml 1,4-dioxane until approximately 20 ml of solution remained. The solution was then cooled to room temperature under $N_2$ and to it was added dried PEG acyl chloride from the above step. After the PEG was dissolved, 0.6 ml dry triethylamine was injected into the system and the reaction mixture was stirred overnight. The salt was filtered from the solution, the solvent condensed on a rotary evaporator, and the syrup was dried in vacuo. The crude product was dissolved in 100 ml distilled water and the pH adjusted to 3.0. The product was extracted three times with a total of 80 ml of methylene chloride. The organic phase was dried over anhydrous sodium sulfate, filtered, condensed under vacuum, and precipitated into 100 ml of ethyl ether. The product was collected by filtration and dried in vacuo. Yield 1.84 g (92%). $^1$H NMR (DMSO-$d_6$): δ 3.5 (br m, PEG), 2.54 (d, PEG-COOCH(CH$_3$)C$\underline{H_2}$COOH), 5.1 (h, PEGCOOCH(CH$_3$)CH$_2$CO$\underline{O}$H), 1.21 (d, PEG-COOCH(C$\underline{H_3}$)CH$_2$COOH), 2.54 (t, PEGOCH$_2$C$\underline{H_2}$COO (PA)), 4.05 (s, $\underline{P}$EGOCH$_2$COO (CM)).

Example 8

Example 8 shows the synthesis of difunctional PEG-HBA—NHS double ester, which can be represented as NHS—OOC—CH$_2$—CH(CH$_3$)—OOC—(CH$_2$)$_n$—O-PEG-O—(CH$_2$)$_n$—COOCH(CH$_3$)CH$_2$—COONHS, for use in preparing PEG hydrogels of the invention. PEG-3-butyric acid (1 g, approx. 0.5 mmole, prepared in example 7) and 64 mg N-hydroxysuccinimide (NHS) (0.53 mmole) were dissolved in 30 ml of dry methylene chloride, followed by addition of dicyclohexylcarbodiimide (DCC, 126 mg, 0.6 mmole) in 5 ml dry methylene chloride. The solution was stirred under nitrogen overnight and the solvent removed by rotary evaporation. The residue was stirred with 10 ml dry toluene at 45° C. and the insoluble solid was removed by filtration. The product was precipitated into 100 ml of dry ethyl ether and the precipitate was collected by filtration and dried in vacuo. Yield 0.94 g (94%). $^1$H NMR(DMSO-$d_6$): δ 3.5 (br m, PEG), 3.0-3.2 (m, —COOCH(CH$_3$)C$\underline{H_2}$COONHS), 5.26 (h, —COOC$\underline{H}$(CH$_3$)CH$_2$COONHS), 1.3 (d, —CO—OCH(C$\underline{H_3}$)CH$_2$C$\underline{O}$ONHS), 2.54 (t, -PEGOCH$_2$C$\underline{H_2}$COO—(PA)), 4.1 (s, -PEGOC$\underline{H_2}$COO—(CM)).

Example 9

Example 9 shows the preparation of a degradable PEG hydrogel from branched PEG amine and the PEG-HBA—NHS double ester of Example 8, which can be represented as NHS—OOC—CH$_2$—CH(CH$_3$)—OOC—(CH$_2$)$_n$—O-PEG-O—(CH$_2$)$_n$—COOCH(CH$_3$)CH$_2$—COONHS. PEG-HBA-NHS double ester 2000 (100 mg, approx. 0.1 mmole, Example 8) was dissolved in 0.5 ml of water and a buffered solution of 8-arm-PEG-amine 10,000 (0.5 ml, 250 mg/ml) was added. After rapid shaking, it was allowed to sit and a gel formed in a few minutes. A suitable buffer pH range was found to be 5.5 to 8.

The invention has been described in particular exemplified embodiments. However, the foregoing description is not intended to limit the invention to the exemplified embodiments, and the skilled artisan should recognize that variations can be mad within the scope and spirit of the invention as described in the foregoing specification. On the contrary, the invention includes all alternatives, modifications, and equivalents that may be included within the true spirit and scope of the invention as defined by the appended claims.

What is claimed is:

1. A crosslinked polymeric structure comprising poly(ethylene glycol) (PEG) polymers in the absence of non-PEG polymers, said PEG polymers crosslinked in the absence of photopolymerization or free-radical polymerization so as to form a solid aggregate and having at least some hydrolytically unstable linkages present in the backbone of said crosslinked PEG polymers that are hydrolyzable under hydrolysis conditions such that the crosslinked polymeric structure is hydrolytically degradable into smaller PEG fragments, said hydrolyzable linkages comprising linkages selected from the group consisting of carboxylate esters, phosphate esters, imines, hydrazones, acetals, and orthoesters, wherein the carboxylate ester is an ester according to the formula —O—(CH$_2$)$_r$—CO$_2$—, wherein r is from 1 to 10, wherein the polymeric structure is in the form of a hydrogel that swells in water.

2. The crosslinked polymeric structure of claim 1 wherein said hydrolytically unstable linkages are sufficient to cause said crosslinked polymeric structure to degrade by hydrolysis.

3. The crosslinked polymeric structure of claim 1 wherein said structure forms a PEG hydrogel that is subject to hydrolysis.

4. The crosslinked polymeric structure of claim 3 wherein the PEG hydrogel formed therefrom has a rate of hydrolysis that is determined at least in part by the structure of said hydrolyzable linkages between said PEG polymers.

5. The crosslinked polymeric structure of claim 4 wherein said hydrolyzable linkages comprise one or more methylene groups sufficient to determine at least in part said rate of hydrolysis of said hydrolytically unstable linkages.

6. The crosslinked polymeric structure of claim 5 wherein said hydrolysis rate is decreased as the number of said methylene groups is increased.

7. The crosslinked polymeric structure of claim 1 wherein said hydrolytically unstable linkages comprise linkages selected from the group consisting of carboxylate esters and phosphate esters.

8. The crosslinked polymeric structure of claim 7 wherein said hydrolytically unstable carboxylate ester linkages are the reaction product of a PEG alcohol and a PEG carboxylic acid and wherein said hydrolytically unstable phosphate ester linkages are the reaction product of a PEG alcohol and a PEG phosphate.

9. A drug delivery system comprising a poly(ethylene glycol) hydrogel made from the crosslinked polymeric structure of claim 1.

10. A crosslinked polymeric structure of claim 1 having a formula selected from the group consisting of:

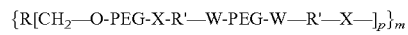

wherein m means "matrix" and indicates that the crosslinked structure is a solid aggregate; p is from about 3 to 10 and indicates the number of arms on the polymers forming said crosslinked structure; R is a central branching moiety; R' is a hydrocarbon fragment having from about 1 to 10 carbons; W is a hydrolytically unstable linkage comprising linkages selected from the group consisting of esters, imines, hydrazones, acetals, and orthoesters, and X is a hydrolytically stable linkage comprising linkages selected from the group consisting of amides, urethanes, ureas, amines, and sulfonamides.

11. The crosslinked polymeric structure of claim 10 wherein R is a moiety selected from the group consisting of glycerol, pentaerythritol, sorbitol, trimethyolpropane, and di(trimethylolpropane).

12. The crosslinked polymeric structure of claim 10 wherein said hydrolytically unstable linkages W comprise carboxylate ester linkages that are the reaction product of an alcohol and a carboxylic acid; phosphate ester linkages that are the reaction product of an alcohol and a phosphate, imine linkages that are the reaction product of an amine and an aldehyde; hydrazones linkages that are the reaction product of a hydrazide and an aldehyde; acetal linkages that are the reaction product of an aldehyde and an alcohol; and orthoester linkages that are the reaction product of a formate and an alcohol.

13. A drug delivery system comprising a poly(ethylene glycol) hydrogel made from the crosslinked polymeric structure of claim 10.

14. A crosslinked polymeric structure comprising poly(ethylene glycol) (PEG) polymers in the absence of non-PEG polymers, said PEG polymers crosslinked in the absence of photopolymerization or free-radical polymerization so as to form a solid aggregate and having at least some hydrolytically unstable linkages between said PEG polymers that are hydrolyzable under hydrolysis conditions, said polymeric structure having the formula:

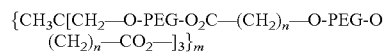

wherein m means "matrix" and indicates that the crosslinked structure is a solid aggregate, and wherein n is from about 1 to 10, wherein the polymeric structure is in the form of a hydrogel that swells in water.

15. The crosslinked polymeric structure of claim 14 wherein when n equals 2, then the ester linkages have a hydrolysis half life of about 4 days at pH7 and 37 degrees Centigrade, and wherein when n equals 3, then the ester linkages have a hydrolysis half life of about 43 days at pH7 and 37 degrees Centigrade.

16. The crosslinked polymeric structure of claim 1 wherein said structure further comprises at least one hydrolytically stable linkage selected from the group consisting of amides, urethanes, ureas, amines, and sulfonamides.

17. A crosslinked polymeric structure of claim 1 having the formula:

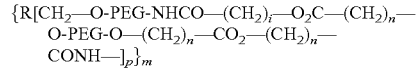

wherein m means "matrix" and indicates that the crosslinked structure is a solid aggregate, n and are each from about 1 to 10, p is from about 3 to 10 and indicates the number of arms on the polymers forming said crosslinked structure, and R is a central branching moiety.

18. A crosslinked polymeric structure of claim 1 having the formula:

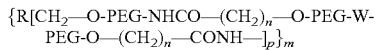

wherein m means "matrix" and indicates that the crosslinked structure is a solid aggregate, n is from about 1 to 10, p is from about 3 to 10 and indicates the number of arms on the polymers forming said crosslinked structure, R is a central branching moiety, and W is a hydrolytically unstable linkage comprising linkages selected from the group consisting of esters, imines, hydrazones, acetals, and orthoesters.

19. A crosslinked polymeric structure of claim 1 having the formula:

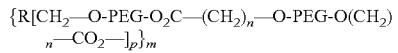

wherein m means "matrix" and indicates that the crosslinked structure is a solid aggregate; p is from about 3 to 10 and indicates the number of arms on the polymers forming said crosslinked structure; R is a central branching moiety selected from the group consisting of glycerol, pentaerythritol, sorbitol, trimethyolpropane, and di(trimethylolpropane); and n is from about 1 to 10.

20. A crosslinked polymeric structure of claim 1 further comprising a biologically active substance.

21. A wound dressing comprising a crosslinked polymeric structure of claim 1.

* * * * *

UNITED STATES PATENT AND TRADEMARK OFFICE
CERTIFICATE OF CORRECTION

| | | |
|---|---|---|
| PATENT NO. | : 7,964,217 B2 | Page 1 of 1 |
| APPLICATION NO. | : 10/684893 | |
| DATED | : June 21, 2011 | |
| INVENTOR(S) | : Harris | |

It is certified that error appears in the above-identified patent and that said Letters Patent is hereby corrected as shown below:

Column 15,

Line 2, "n and are each" should read --n and i are each--.

Signed and Sealed this
Seventh Day of February, 2012

David J. Kappos
*Director of the United States Patent and Trademark Office*